United States Patent
Bossenmaier et al.

(10) Patent No.: US 7,163,953 B2
(45) Date of Patent: Jan. 16, 2007

(54) BENZYLETHER DERIVATIVES

(75) Inventors: Birgit Bossenmaier, Seefeld (DE); Walter-Gunar Friebe, Mannheim (DE); Thomas Friess, Planegg (DE); Christian Geletneky, Starnberg (DE); Guy Georges, Habach (DE); Irene Kolm, Weilheim (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/131,576

(22) Filed: May 18, 2005

(65) Prior Publication Data

US 2005/0267178 A1 Dec. 1, 2005

(30) Foreign Application Priority Data

May 25, 2004 (EP) .................................. 04012295

(51) Int. Cl.
*A61K 31/422* (2006.01)
*C07D 263/30* (2006.01)
*C07D 413/12* (2006.01)

(52) U.S. Cl. ..................... 514/374; 548/215; 548/235

(58) Field of Classification Search ................ 548/215, 548/235; 514/374
See application file for complete search history.

(56) References Cited

FOREIGN PATENT DOCUMENTS

| EP | 1270571 | 1/2003 |
|---|---|---|
| WO | WO 98/03505 | 1/1998 |
| WO | WO 01/77107 | 10/2001 |
| WO | WO 03/031442 | 4/2003 |
| WO | WO 03/059907 | 7/2003 |

OTHER PUBLICATIONS

Tasaka et al (2003), STN International CAPLUS database, Columbus (Ohio), accession No. 2003: 570981.*
Wilks et al., Progress in Growth Factor Research, 2, pp. 97-111 (1990).
Chan et a., Cur. Opin. in Immunol., 8, pp. 394-401 (1995).
Yarden et al., Ann. Rev. Biochem., 57, pp. 443-478 (1988).
Wright et al., Br. J. Cancer, 65, pp. 118-121 (1992).
Baselga et al., Oncology, 63 (Suppl. 1), pp. 6-16 (2002).
Ranson et al., Oncology, 63 (Suppl. 1), pp. 17-24 (2002).
Bastin et al., Organic Proc. Res. Dev., 4, pp. 427-435 (2000).

* cited by examiner

*Primary Examiner*—Golam M. M. Shameem
(74) *Attorney, Agent, or Firm*—George W. Johnston; Patricia S. Rocha-Tramaloni; Brian C. Remy

(57) ABSTRACT

Objects of the present invention are the compounds of formula (I)

formula (I)

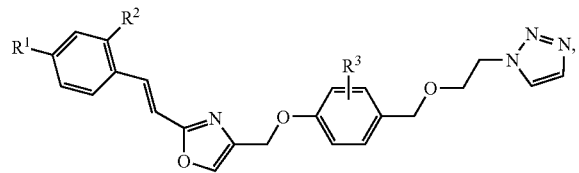

their pharmaceutically acceptable salts or esters, enantiomeric forms, diastereoisomers and racemates, the preparation of the above-mentioned compounds, pharmaceutical compositions containing them and their manufacture, as well as the use of the above-mentioned compounds in the control or prevention of illnesses such as cancer.

11 Claims, No Drawings

BENZYLETHER DERIVATIVES

PRIORITY TO RELATED APPLICATIONS

This application claims the benefit of European Application No. 04012295.4, filed May 25, 2004, which is incorporated herein by reference in its entirety.

FIELD OF THE INVENTION

The present invention relates to novel benzylether derivatives, to a process for their manufacture, pharmaceutical compositions containing them and their manufacture as well as the use of such compounds as pharmaceutically active agents.

BACKGROUND OF THE INVENTION

Protein tyrosine kinases (PTKs) catalyse the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394–401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443–478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer (colon, rectal or stomach cancer), leukemia and ovarian, bronchial and pancreatic cancer. High levels of these receptors correlate with poor prognosis and response to treatment (Wright, C., et al., Br. J. Cancer 65 (1992) 118–121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6–16; Ranson, M., and Sliwkowski, M. X., Oncology 63 (suppl. 1) (2002) 17–24).

Some substituted oxazoles are known in the art. WO 98/03505, EP 1 270 571, WO 01/77107, WO 03/031442 and WO 03/059907 disclose related heterocyclic compounds as -tyrosine kinase inhibitors.

However there remains a need for new compounds with improved therapeutic properties, such as enhanced activity, decreased toxicity, better solubility and improved pharmacokinetic profile, to name only a few.

SUMMARY OF THE INVENTION

The present invention relates to compounds of the general formula I and pharmaceutically acceptable salts or esters thereof, wherein formula I is:

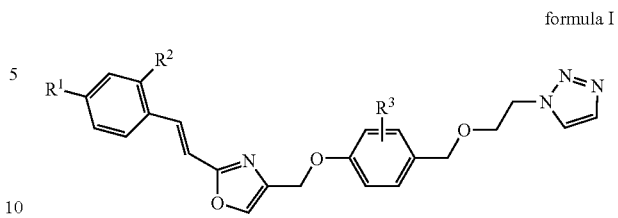

formula I wherein:
(a) $R^1$ is selected from the group consisting of:
  (1) chlorine; and
  (2) fluorine
(b) $R^2$ is selected from the group consisting of:
  (1) hydrogen; and
  (2) fluorine; and
(c) $R^3$ is selected from the group consisting of:
  (1) hydrogen;
  (2) halogen;
  (3) alkyl; and
  (4) alkoxy.

The compounds of formula I are useful for preventing or treating proliferative diseases and conditions such as tumor growth and cancer including, but not limited to, breast cancer, leukemia, ovarian cancer, bronchial or lung cancer, pancreatic cancer, and gastrointestinal cancer such as colon cancer, rectal cancer, and stomach cancer.

The compounds of the present invention show activity as inhibitors of the HER-signalling pathway and therefore possess anti-proliferative activity. The present invention provides the compounds of formula I and their pharmaceutically acceptable salts or esters, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above such as common human cancers (e.g. breast cancer, gastrointestinal cancer (colon, rectal or stomach cancer), leukemia and ovarian, bronchial and pancreatic cancer) or in the manufacture of corresponding pharmaceutical compositions.

DETAILED DESCRIPTION OF THE INVENTION

As used herein, the term "alkyl" means a saturated, straight-chain or branched-chain hydrocarbon containing from 1 to 4, preferably 1 to 2, carbon atoms, such as methyl, ethyl, n-propyl, isopropyl, n-butyl, sec-butyl, tert-butyl.

As used herein, the term "alkoxy" means an alkyl group as defined above, which is attached via an oxygen atom, such as methoxy, ethoxy, n-propoxy, isopropoxy, n-butoxy, sec-butoxy, tert-butoxy.

The term "halogen" as used herein denotes fluorine, chlorine or bromine, preferably fluorine or chlorine, more preferably fluorine.

As used herein, when referring to the receptor tyrosine kinases of the HER-family like HER-2 and EGFR (HER-1), the acronym "HER" refers to human epidermal receptor and the acronym "EGFR" refers to epidermal growth factor receptor.

As used herein, in relation to mass spectrometry (MS) the term "ESI+" refers to positive electrospray ionization mode and the term "API+" refers to positive atmospheric pressure ionization mode.

As used herein, "THF" refers to tetrahydrofuran.

As used herein, "EGTA" refers to ethylene glycol-bis(2-aminoethylether)-N,N,N',N'-tetraacetic acid.

As used herein, "PMSF" refers to phenylmethylsulfonyl fluoride.

As used herein, "DMSO" refers to N,N-dimethylsulfoxide.

As used herein, the term "DMF" refers to N,N-dimethyl formamide.

As used herein, "Hepes" refers to 4-(2-Hydroxyethyl)-1-piperazineethanesulfonic acid.

As used herein, in relation to nuclear magnetic resonance (NMR) the term "$D_6$-DMSO" refers to deuterated N,N-dimethylsulfoxide.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The compounds according to the present invention may exist in the form of their pharmaceutically acceptable salts or esters. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g. Bastin, R. J. et al, Organic Proc. Res. Dev. 4 (2000) 427–435.

Preferred are the pharmaceutically acceptable salts, which are formed with p-toluenesulfonic acid, naphthalenesulfonic acid, naphthalenedisulfonic acid, methanesulfonic acid and hydrochloric acid.

In a preferred embodiment, $R^1$ in formula I is chlorine.

In another preferred embodiment $R^3$ in formula I is hydrogen, methyl, methoxy, fluorine, or chlorine.

A preferred embodiment of the invention are the compounds of formula I, wherein $R^1$ is chlorine.

Such a compound is for example:
1-[2-(4-{2-[2-(4-Chloro-phenyl)-vinyl]-oxazol-4-yl-methoxy}-benzyloxy)-ethyl]-1H-[1,2,3]triazole.

A preferred embodiment of the present invention is the compound:
1-[2-(4-{2-[2-(4-Chloro-2-fluoro-phenyl)-vinyl]-oxazol-4-ylmethoxy}-benzyloxy)-ethyl]-1H-[1,2,3]triazole.

Another preferred embodiment are the compounds of formula I, wherein $R^1$ is fluorine.

Still another preferred embodiment are the compounds of formula I, wherein $R^1$ is chlorine and $R^3$ is hydrogen.

Another preferred embodiment are the compounds of formula I, wherein $R^2$ is hydrogen.

Another preferred embodiment are the compounds of formula I, wherein $R^2$ is fluorine.

Another preferred embodiment are the compounds of formula I, wherein $R^3$ is hydrogen.

Still a preferred embodiment of the invention are the compounds of formula I, wherein $R^3$ is alkyl.

Another preferred embodiment are the compounds of formula I, wherein $R^3$ is alkoxy.

Another preferred embodiment are the compounds of formula I, wherein $R^3$ is halogen.

Another preferred embodiment are the compounds of formula I, wherein $R^3$ is fluorine.

Another preferred embodiment are the compounds of formula I, wherein $R^3$ is chlorine.

Still another embodiment of the invention is a process for the manufacture of the compounds of formula I, wherein:
(a) the compound of formula V

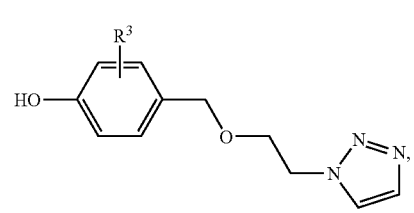

formula V wherein $R^3$ has the significance given herein above for formula I, is reacted with a compound of formula IV

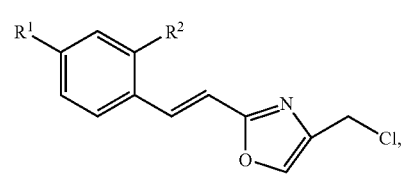

formula IV wherein $R^1$ and $R^2$ have the significance given herein above for formula I, to give the respective compound of formula I;
(b) said compound of formula I is isolated from the reaction mixture, and
(c) optionally, converted into a pharmaceutically acceptable salt or ester.

The benzylether derivatives of the general formula I, or a pharmaceutically acceptable salt or ester thereof, may be prepared by any process known to be applicable for the preparation of chemically-related compounds by the one skilled in the art. Such processes, when used to prepare the benzylether derivatives of formula I, or a pharmaceutically-acceptable salt or ester thereof, are provided as a further feature of the invention and are illustrated by the following representative examples of scheme 1, in which, unless otherwise stated $R^1$, $R^2$ and $R^3$ have the significance given herein before. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

A preferred method for the synthesis of the compounds of formula I is described in scheme 1, and starts from the corresponding benzaldehydes of formula Ia, wherein $R^1$ and $R^2$ have the significance given above for formula I. The first step of the reaction sequence is a Knoevenagel condensation with malonic acid and concomitant decarboxylation, yielding acrylic acids of formula II. The reaction is typically carried out in solvents like pyridine, N-methylpyrrolidinone (NMP), acetonitrile, N,N-dimethylformamide (DMF) and mixtures thereof at temperatures up to 140° C. Typically used bases are piperidine, triethylamine and diisopropylamine.

The obtained acrylic acids of formula II are converted into their corresponding amides of formula III by standard methods for someone skilled in the art, e.g. by activating the carboxylic group in formula II with oxalyl chloride in solvents like tetrahydrofuran (THF), dichloromethane, DMF and mixtures thereof at temperatures varying from −30° C. to 40° C. The addition of ammonia yields said amides of formula III.

Chlorides of formula IV can be synthesized by a commonly known method or a modification thereof. Amides of formula III and 1,3-dichloroacetone are subjected to a condensation/dehydration sequence yielding the compounds of formula IV. Typical solvents for reactions of this kind are Scheme 1

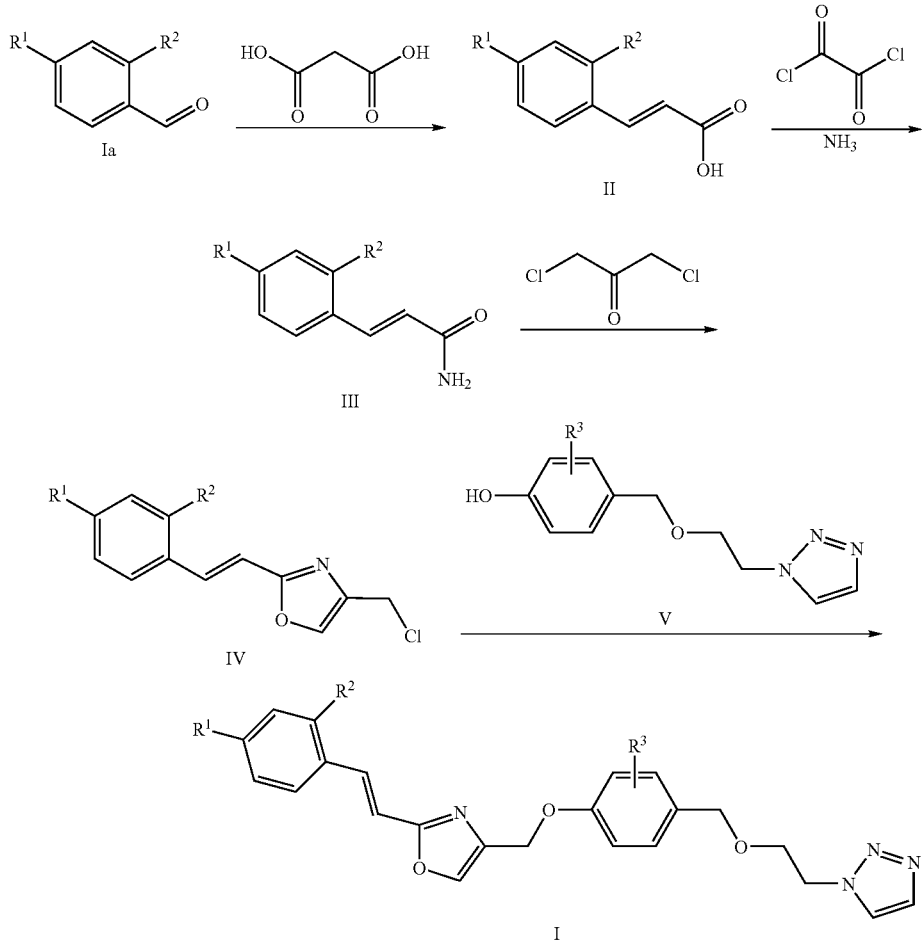

toluene, xylene, benzene, acetone and chloroform. If desired, the reaction can be carried out under solvent free conditions. The reaction temperatures may vary from 50° C. to 150° C.

The benzylether derivatives of formula I can be obtained by reactions well known to someone skilled in the art, e.g. by alkylation of compounds of formula V, wherein $R^3$ has the significance given above for formula I, with compounds of formula IV according to scheme 1. Typically the alkylation is carried out in the presence of potassium iodide or sodium iodide in solvents like DMF, methanol, ethanol and isopropanol. Typical bases for this reaction are sodium methylate, sodium hydride or lithium diisopropyl amide. The reaction temperatures may vary from 50° C. to 150° C.

The phenolic intermediate of formula V may be prepared by reaction of a compound of formula VI with a compound of formula VII

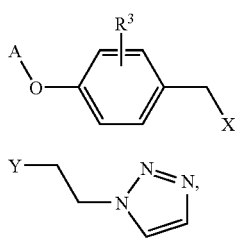

formula VI formula VII wherein
A denotes a suitable protecting group as defined below, and
one of X and Y denotes a hydroxy group,
while the other denotes a suitable leaving group E as defined below,
and subsequent removal of the protecting group A.

Reactions of compounds of formula VI with compounds of formula VII are well known in the art. Typically, such alkylation reaction may be carried out in solvents like DMF, methanol, ethanol and isopropanol. Typical bases for this reaction are alkaline carbonates, sodium methylate, sodium hydride or lithium diisopropyl amide. The reaction temperatures may vary from 20° C. to 150° C. Other preferred alkylation procedures make use of alkaline carbonates as bases in solvents like ketones, for example cesium carbonate in butanone at reflux temperature, or sodium hydride in DMF at room temperature. Suitable leaving groups E are those typically used in alkylation reactions and well known to the skilled artisan. Examples of such leaving groups are, among others, the anions of halogens, especially iodide, bromide or chloride, p-toluenesulfonate (tosylate), methanesulfonate (mesylate), trifluoromethansulfonate (triflate) or the azido group.

The hydroxy protecting group A as mentioned herein is a conventional protecting group as known by the skilled artisan. Examples are tert-butoxycarbonyl (boc), propen-3-yl (allyl), triphenylmethyl (trityl) and silyl groups, e.g. tert.-butyl-dimethyl-silyl, triisopropyl-silyl.

Removal of a protecting group on a hetero atom depends on the nature of such group. Typical examples are the removal of a trityl group under acidic conditions, for example with aqueous formic acid in tetrahydrofuran (THF) under reflux or the removal of a tert-butoxycarbonyl group with trifluoroacetic acid in dichloromethane at room temperature or the removal of a substituted silyl group with tetrabutylammonium fluoride in aqueous THF at room temperature. An allyl group can smoothly be removed by treating the substrate with catalytic amounts of a palladium complex, e.g. $Pd(PPh_3)_4$ in dichloromethane in the presence of an allyl-acceptor such as 1,3-dimethylbarbituric acid.

Compounds of formula V are new and also the subject of this invention.

The compounds of formula I can contain a chiral center and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

The compounds of formula I and their pharmaceutically acceptable salts or esters possess valuable pharmacological properties. It has been found that said compounds inhibit the HER-signalling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above. The activity of the present compounds as HER-signalling pathway inhibitors is demonstrated by the following biological assay:

Inhibition of HER-2 Phosphorylation in Calu-3 Tumor Cell Line $2\times10^5$ Calu-3 cells (Non-Small-Cell Lung Cancer cells, ATTC HTB-55) per well were plated in a 12-well plate. After 4 days cells were starved for 16 h in Dulbecco's Modified Eagle Medium (DMEM)/0.5% Fetal Calf Serum (FCS)/1% Glutamine. During this 16 h period cells were incubated with a solution of the test compound in dimethylsulfoxide (DMSO), so that the final concentration of the compound is 1 μM and the final volume of DMSO is 0.5%. Afterwards cells were lysed in lyses buffer containing 1% octyl phenol ethoxylate (Triton®X-100), 10% Glycerol, 1 mM Ethylene glycol-bis(2-aminoethylether)-N,N,N',N'-tetraacetic acid (EGTA), 1.5 mM $MgCl_2$, 150 mM NaCl, 50 mM 4-(2-hydroxyethyl)-1-piperazineethanesulfonic acid (HEPES) buffer pH 7.5, 1 mM Phenylmethylsulfonyl fluoride (PMSF), 10 μg/mL Aprotinin (naturally occurring protein that is obtained and purified from cow's lungs) and 0.4 mm Orthovanadate ($Na_3VO_4$). Cell lysates were analyzed on a Sodium Dodecyl Sulfate Polyacrylamide Gel Electrophoresis (SDS PAGE) and after transfer to a nitrocellulose membrane detected with an antibody specifically recognizing the pY 1248 in HER-2 (phosphorylated tyrosine residue 1248 of human epidermal receptor 2). After incubation with an anti rabbit antibody coupled to POD (peroxidase available from Biorad, Munich, Germany) signals were detected by chemiluminescence (ECL, Amersham). Inhibition of HER-2 phosphorylation is calculated as a percentage of the control, which is treated with DMSO only. The percentage of the inhibition is calculated according to the following formula: Inhibition in %=100−(Phosphorylated-HER2-Signal of Test Sample* 100/Phosphorylated-HER2-Signal DMSO-control).

With all compounds a significant inhibition of HER-2-phosphorylation was detected, which is exemplified by the compounds shown in Table 1. The reference compound as used herein is 1-[4-(4-{2-[2-(4-Trifluoromethyl-phenyl)-vinyl]-oxazol-4-ylmethoxy}-phenyl)-butyl]-1H-[1,2,3]triazole (Example 4, p. 88, WO 01/77107).

TABLE 1

| | Control (DMSO) | Percent inhibition of HER-2-phosphorylation (compound concentration 1 μM) |
|---|---|---|
| reference compound | 0 | 52.3 |
| example 1 | 0 | 65–80 |
| example 2 | 0 | >80 |

In Vivo Assay on Tumor Inhibition:

To generate primary tumors, Non-Small-Cell Lung Cancer (NSCLC) (e.g. Calu-3 (ATTC HTB-55) or A549 (ATTC CCL-185)) cells (4–5.0×10$^6$ in a volume of 100 μl) are injected subcutaneously into the left flank of female SCID beige (Severe Combined Immunodeficient/beige mice available from Charles River, Sulzfeld, Germany) or BALB/c nude (BALB/c Nude Spontaneous Mutant Mice (homozygotes) available from Taconic Europe, Ry, Denmark) mice. The cells are thawed and expanded in vitro before use in the experiment. Mice are assigned to the treatment groups 14–21 days after cell injection. For grouping (n=10–15 mice per group), the animals are randomized to get a similar mean primary tumor volume of ca. 100–150 mm$^3$ per group. The test compounds are administered orally once per day as a suspension in 7.5% gelatine 0.22% NaCl with an administration volume of 10 ml/kg based on actual body weights. Treatment is initiated one day after staging, and carried out until day 20–50, the final day of the study. The subcutaneous primary tumors are measured twice weekly, starting prior to randomisation, in two dimensions (length and width) using an electronic caliper. The volume of the primary tumor is calculated using the formula: V[mm$^3$]=(length [mm]×width [mm]×width [mm])/2. In addition, the body weight of all animals is recorded at least twice weekly. Finally, at the end of the study the tumors are explanted and weighed.

The compounds according to this invention and their pharmaceutically acceptable salts or esters can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. For example, lactose, corn starch or derivatives thereof, talc, stearic acids or it's salts and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions comprise e.g. the following:

a) Tablet Formulation (Wet Granulation):

| Item | Ingredients | Mg/tablet | | | |
|---|---|---|---|---|---|
| 1. | Compound of formula I | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro Suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I-A with particle sizes between 1 and 10 μm. The suspensions are suitable for oral applications and can be used in the in vivo assay described above.

Pharmaceutical compositions containing a compound of the present invention or a pharmaceutically acceptable salt or ester thereof and a therapeutically inert carrier are also an object of the present invention, as is a process for their production, which comprises bringing one or more compounds of the present invention and/or pharmaceutically acceptable salts or esters and, if desired, one or more other therapeutically valuable substances into a galenical administration form together with one or more therapeutically inert carriers.

In accordance with the invention the compounds of the present invention as well as their pharmaceutically acceptable salts or esters are useful in the control or prevention of illnesses. Based on their HER-signalling pathway inhibition and their antiproliferative activity, said compounds are useful for the treatment of diseases such as cancer in humans or animals and for the production of corresponding pharmaceutical compositions. The dosage depends on various factors such as the manner of administration, species, age and/or individual state of health.

Another embodiment of the invention is a pharmaceutical composition, containing one or more compounds of formula I together with pharmaceutically acceptable excipients.

Still another embodiment of the invention is said pharmaceutical composition for the inhibition of tumor growth.

Still another embodiment of the invention is the use of a compound of formula I for the treatment of cancer.

Still another embodiment of the invention is the use of a compound of formula I for the manufacture of corresponding pharmaceutical compositions for the inhibition of tumor growth.

The following examples and references are provided to aid the understanding of the present invention, the true scope of which is set forth in the appended claims. It is understood that modifications can be made in the procedures set forth without departing from the spirit of the invention.

EXAMPLES

Example 1

1-[2-(4-{2-[2-(E)-(4-Chloro-2-fluoro-phenyl)-vinyl]-oxazol-4-ylmethoxy}-benzyloxy)-ethyl]-1H-[1,2,3]triazole To a suspension of 49.0 g (244 mmol) 3-(4-chloro-2-fluoro-phenyl)-acrylic acid in 300 ml tetrahydrofuran and 2.8 ml N,N-dimethylformamide a solution of 26.2 ml (305 mmol) oxalyl chloride in 50 ml tetrahydrofuran was added dropwise at 0° C. within 45 min. Stirring was continued at 0–5° C. for 30 min. and 2 h at room temperature thereafter. The resulting solution was cooled to 0–5° C. again and then added within 15 min. to 750 ml of a 25% aqueous ammonia solution. Tetrahydrofuran was distilled off in vacuo, precipitated amide was collected, washed with water and heptane, then dried at 40° C. in vacuo. Yield: 45.9 g (94%) 3-(4-Chloro-2-fluoro-phenyl)-acrylamide.

$^1$H-NMR (400 MHz, D$_6$-DMSO): δ=6.72 (d, 1H, 2-H), 7.23 (br, 1H, NH), 7.35 (d, 1H, 5'-H), 7.44 (d, 1H, 3-H), 7.50 (d, 1H, 3'-H), 7.68 (br, 1H, NH), 7.95 (dd, 1H, 6'-H).

45.0 g (225 mmol) 3-(4-Chloro-2-fluoro-phenyl)-acrylamide, 35.5 g (280 mmol) 1,3-dichloroacetone and 500 ml toluene were kept at reflux temperature for 24 h with continuous removal of water by use of a water separator used in chemical reactions (Dean-Stark trap). After cooling to room temperature and two washings with 80 ml water, the organic phase was dried over sodium sulphate and the solvent removed in vacuo. The residue was stirred with 80 ml methanol for 30 min., the precipitate filtered, washed with cold methanol, stirred with n-heptane, sucked off and dried in vacuo at 40° C. Yield: 28.9 g (47%) 2-[2-(4-Chloro-2-fluoro-phenyl)-vinyl]-4-chloromethyl-oxazole.

$^1$H-NMR (400 MHz, D$_6$-DMSO): δ=6.72 (d, 1H, 1'-H), 7.35 (d, 1H, 5''-H), 7.44 (d, 1H, 2'-H), 7.50 (d, 1H, 3''-H), 7.95 (dd, 1H, 6''-H), 8.21 (s, 1H, 5-H-oxazole).

380 mg (15 mmol) of 95% sodium hydride were given to a solution of 3.00 g (13.7 mmol) 4-(2-[1,2,3]triazol-1-yl-ethoxymethyl)-phenol in 70 ml N,N-dimethylformamide and stirred for 30 min at room temperature. Then 3.73 g (13.7 mmol) 2-[2-(4-chloro-2-fluoro-phenyl)-vinyl]-4-chloromethyl-oxazole were added and stirring continued over night. The mixture was quenched with water, stirred for 1 h and the precipitate isolated by filtration. After washing with water, little methanol, ethyl acetate/heptane 2:1 and ether, and drying at 40° C. in vacuo, 3.34 g (54%) 1-[2-(4-{2-[2-(E)-(4-chloro-2-fluoro-phenyl)-vinyl]-oxazol-4-yl-methoxy}-benzyloxy)-ethyl]-1H-[1,2,3]triazole were obtained.

MS: M=455.1 (ESI+). $^1$H-NMR (400 MHz, D$_6$-DMSO): δ=3.79 (t, 2H, C$\underline{H}_2$—CH$_2$-triazole), 4.40 (s, 2H, OCH$_2$—Ph), 4.57 (t, 2H, CH$_2$-triazole), 5.01 (s, 2H, OCH$_2$-oxazole), 6.98 (d, 2H, Ar—H), 7.17 (d, 2H, Ar—H) 7.24 (d, 1H, vinyl-H), 7.35 (d, 1H, Ar—H), 7.52 (d, 1H, vinyl-H), 7.53 (d, 1H, Ar—H), 7.72 (s, 1H, triazole), 7.93 (dd, 1H, Ar—H), 8.08 (s, 1H, triazole), 8.23 (s, 1H, oxazole).

Example 2

1-[2-(4-{2-[2-(E)-(4-Chloro-phenyl)-vinyl]-oxazol-4-ylmethoxy}-benzyloxy)-ethyl]-1H-[1,2,3]triazole 25 mg (1.0 mmol) of 95% sodium hydride were given to a solution of 219 mg (1.0 mmol) 4-(2-[1,2,3]triazol-1-yl-ethoxymethyl)-phenol in 5 ml N,N-dimethylformamide and stirred for 15 min at room temperature. Then 254 mg (1.0 mmol) 2-[2-(4-chloro-phenyl)-vinyl]-4-chloromethyl-oxazole were added and stirring continued over night. The mixture was quenched with water, stirred for 1 h and the precipitate isolated by filtration. After washing with water, little methanol, ethyl acetate/heptane 2:1 and ether, and drying at 40° C. in vacuo, 341 mg (78%) 1-[2-(4-{2-[2-(E)-(4-chloro-phenyl)-vinyl]-oxazol-4-ylmethoxy}-benzyloxy)-ethyl]-1H-[1,2,3]triazole were obtained.

MS: M=437.3 (API+). $^1$H-NMR (400 MHz, D$_6$-DMSO): δ=3.80 (t, 2H, C$\underline{H}_2$—CH$_2$-triazole), 4.40 (s, 2H, OCH$_2$—Ph), 4.58 (t, 2H, CH$_2$-triazole), 5.01 (s, 2H, OCH$_2$-oxazole), 7.00 (d, 2H, Ar—H), 7.17 (d, 2H, Ar—H) 7.18 (d, 1H, vinyl-H), 7.48 (d, 2H, Ar—H), 7.53 (d, 1H, vinyl-H), 7.74 (d, 2H, Ar—H), 7.75 (s, 1H, triazole), 8.08 (s, 1H, triazole), 8.21 (s, 1H, oxazole).

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. Compounds of formula I and pharmaceutically acceptable salts or esters thereof wherein formula I is:

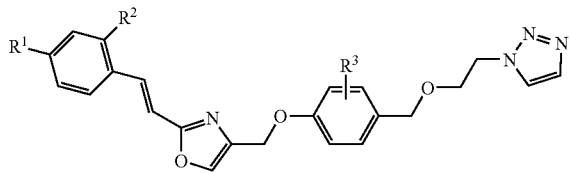

formula I wherein:
(a) $R^1$ is selected from the group consisting of:
  (1) chlorine; and
  (2) fluorine;
(b) $R^2$ is selected from the group consisting of:
  (1) hydrogen; and
  (2) fluorine; and
(c) $R^3$ is selected from the group consisting of:
  (1) hydrogen;
  (2) halogen;
  (3) alkyl; and
  (4) alkoxy.

2. The compounds according to claim 1, wherein $R^1$ is chlorine.

3. A compound according to claim 2 selected from the group consisting of:
  (a) 1-[2-(4-{2-[2-(4-Chloro-phenyl)-vinyl]-oxazol-4-yl-methoxy}-benzyloxy)-ethyl]-1H-[1,2,3]triazole; and
  (b) 1-[2-(4-{2-[2-(4-Chloro-2-fluoro-phenyl)-vinyl]-oxazol-4-ylmethoxy}-benzyloxy)-ethyl]-1H-[1,2,3]triazole.

4. The compounds according to claim 1, wherein $R^1$ is fluorine.

5. The compounds according to claim 1, wherein $R^2$ is hydrogen.

6. The compounds according to claim 1, wherein $R^2$ fluorine.

7. The compounds according to claim 1, wherein $R^3$ is hydrogen.

8. The compounds according to claim 1, wherein $R^3$ is alkyl.

9. The compounds according to claim 1, wherein $R^3$ is halogen.

10. The compounds according to claim 1, wherein $R^3$ is alkoxy.

11. A pharmaceutical composition comprising a therapeutically effective amount of the compound of claim 1 and a pharmaceutically acceptable carrier.

* * * * *